(12) United States Patent
Woo et al.

(10) Patent No.: US 9,049,980 B2
(45) Date of Patent: Jun. 9, 2015

(54) STRAIN RELIEF APPARATUS FOR PROBE AND METHOD OF MANUFACTURING THE SAME

(75) Inventors: Kyeong Gu Woo, Suwon-si (KR); Sun Ki Lee, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 1239 days.

(21) Appl. No.: 12/949,651

(22) Filed: Nov. 18, 2010

(65) Prior Publication Data

US 2011/0123256 A1    May 26, 2011

(30) Foreign Application Priority Data

Nov. 20, 2009   (KR) .................. 10-2009-0112496

(51) Int. Cl.
| | |
|---|---|
| A61B 8/14 | (2006.01) |
| A61B 8/00 | (2006.01) |
| A61B 8/12 | (2006.01) |
| H01B 17/26 | (2006.01) |
| H01B 17/58 | (2006.01) |
| H02G 3/22 | (2006.01) |
| H01B 7/00 | (2006.01) |

(52) U.S. Cl.
CPC ... *A61B 8/00* (2013.01); *A61B 8/44* (2013.01); *A61B 8/4455* (2013.01); *A61B 8/12* (2013.01)

(58) Field of Classification Search
CPC ........... A61B 8/12; A61B 8/44; A61B 8/4455
USPC ....... 174/152 R, 153 G, 152 G, 135; 600/459
See application file for complete search history.

(56) References Cited

U.S. PATENT DOCUMENTS

| | | | | |
|---|---|---|---|---|
| 5,368,036 A | * | 11/1994 | Tanaka et al. | ................. 600/462 |
| 5,630,419 A | | 5/1997 | Ranalletta | |
| 5,678,551 A | | 10/1997 | Stevens | |
| 5,827,175 A | * | 10/1998 | Tanaka | .......................... 600/104 |
| 6,142,947 A | | 11/2000 | Tran et al. | |
| 2010/0193220 A1 | * | 8/2010 | Prasad et al. | .................. 174/135 |

FOREIGN PATENT DOCUMENTS

| | | |
|---|---|---|
| JP | 2-191447 A | 7/1990 |
| JP | 11-347031 A | 12/1999 |
| JP | 2009-110888 A | 5/2009 |

OTHER PUBLICATIONS

Japanese Office issued on Aug. 19, 2014 in Japanese Patent Application No. 2010-255245.
Korean Office Action dated Jul. 13, 2011 issued Korean Application No. 10-2009-0112496.
European Search Report issued in European Patent Application No. 10187713.2-2319, mailed Mar. 2, 2011.

* cited by examiner

*Primary Examiner* — Hoa C Nguyen
*Assistant Examiner* — Binh Tran
(74) *Attorney, Agent, or Firm* — McDermott Will & Emery LLP

(57) ABSTRACT

A strain relief apparatus of a probe and a method of manufacturing the same are disclosed. The strain relief apparatus includes an insert part mounted on a probe switch box and having an insertion recess at an inner side thereof, a ferrite core mounted on the insertion recess, and a rubber part provided to the insert part by injection molding. The strain relief apparatus protects a cable of an ultrasonic diagnostic apparatus from impact exerted on the cable and suppresses influence on a contact point between a probe switch box and the cable by bending of the cable, thereby preventing damage of the cable.

3 Claims, 3 Drawing Sheets

STRAIN RELIEF APPARATUS FOR PROBE AND METHOD OF MANUFACTURING THE SAME

CROSS REFERENCE TO RELATED APPLICATIONS

This application claims the benefit of Korean Patent Application No. 10-2009-0112496, filed on Nov. 20, 2009, the entire contents of which are incorporated herein by reference.

BACKGROUND OF THE INVENTION

1. Field of the Invention

The present invention relates to a strain relief apparatus and, more particularly, to a strain relief apparatus for a probe and a method of manufacturing the same.

2. Description of the Related Art

Generally, an ultrasonic diagnostic apparatus refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasonic diagnostic apparatus has been widely used for diagnosis of the heart, the abdomen, the urinary organs, and in obstetrics and gynecology due to various merits thereof such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

Particularly, the ultrasonic diagnostic apparatus includes a probe which transmits an ultrasound signal to a target and receives the ultrasound echo-signal reflected therefrom to obtain an ultrasound internal image of the target.

The probe includes a transducer. The transducer transmits an ultrasound signal to the target and receives the ultrasound echo-signal reflected therefrom using a piezoelectric layer in which a piezoelectric material converts electrical signals into sound signals or vice versa through vibration thereof.

When using the apparatus for ultrasound diagnosis of a target, an operator moves or rotates the probe with one hand while keeping the probe in contact with a surface of the target to obtain an ultrasound image of the target.

A cable is connected to the rear side of the probe. The probe is connected to a main body of the ultrasonic diagnostic apparatus via a cable that is connected to the main body of the ultrasonic diagnostic apparatus.

The cable connecting the probe to the main body of the apparatus is connected to a printed circuit board (PCB), which is connected to the transducer, through a case of the probe, and is bonded to the case at a contact point with the case by an adhesive or the like, so that the cable is provided to the probe.

It should be noted that the above description is provided for understanding of the background of the invention and is not a description of a conventional technique well-known in the art.

The cable provided to the probe is likely to be bent during the movement or use of the probe. Then, the bending of the cable may cause a force at the contact point between the cable and the case, and may break the cable. Therefore, there is a need to solve such a problem.

SUMMARY OF THE INVENTION

The present invention is conceived to solve the problem of the related art, and an aspect of the invention is to provide a strain relief apparatus of a probe and a method of manufacturing the same that can reduce influence by bending of a cable.

In accordance with one aspect of the invention, a strain relief apparatus of a probe includes: an insert part mounted on a probe switch box and having an insertion recess at an inner side thereof; a ferrite core mounted on the insertion recess; and a rubber part provided to the insert part by injection molding.

The insert part may include an extension portion extending towards the rubber part to define the insertion recess inside the extension portion.

The extension portion may be formed with an injection groove and the rubber part may be formed on the extension portion and the injection groove by insert-injection molding.

The rubber part may be provided to the insert part without a step therebetween by the injection molding.

The apparatus may further include a D-cut portion formed on one side of the insert part to prevent rotation of the insert part mounted on the probe switch box.

In accordance with another aspect of the invention, a method of manufacturing a strain relief apparatus of a probe includes: preparing an insert part; inserting a ferrite core into the insert part; and insert-injection molding a rubber part to the insert part with the ferrite core inserted therein.

The preparation of an insert part may include forming an injection groove to which the rubber part is formed by the insert-injection molding.

The preparation of an insert part may include forming a D-cut portion on the insert part.

According to one embodiment of the invention, the strain relief apparatus protects a cable of an ultrasonic diagnostic apparatus from impact exerted on the cable and suppresses influence on a contact point between a probe switch box and the cable by bending of the cable, thereby preventing damage of the cable.

Further, according to the embodiment, the rubber part is formed by insert-injection molding to the insert part with the ferrite core inserted into the insert part, so that the number of components is reduced and separate assembly operation is eliminated, thereby facilitating the fabrication of the apparatus and reducing manufacturing costs.

Moreover, according to the embodiment, the insert part is prevented from rotating on the probe switch box and the rubber part is prevented from rotating on the insert part, thereby preventing abrasion or damage of the strain relief apparatus caused by rotation and friction between the probe switch box, insert part and rubber part.

BRIEF DESCRIPTION OF THE DRAWINGS

The above and other aspects, features and advantages of the invention will become apparent from the following description of embodiments given in conjunction with the accompanying drawings, in which.

DETAILED DESCRIPTION OF THE EMBODIMENT

Embodiments of the invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the invention into account and can be changed according to the custom or intention of users or operators. Therefore, definition of the terms should be made according to overall disclosures set forth herein.

Figure 1:
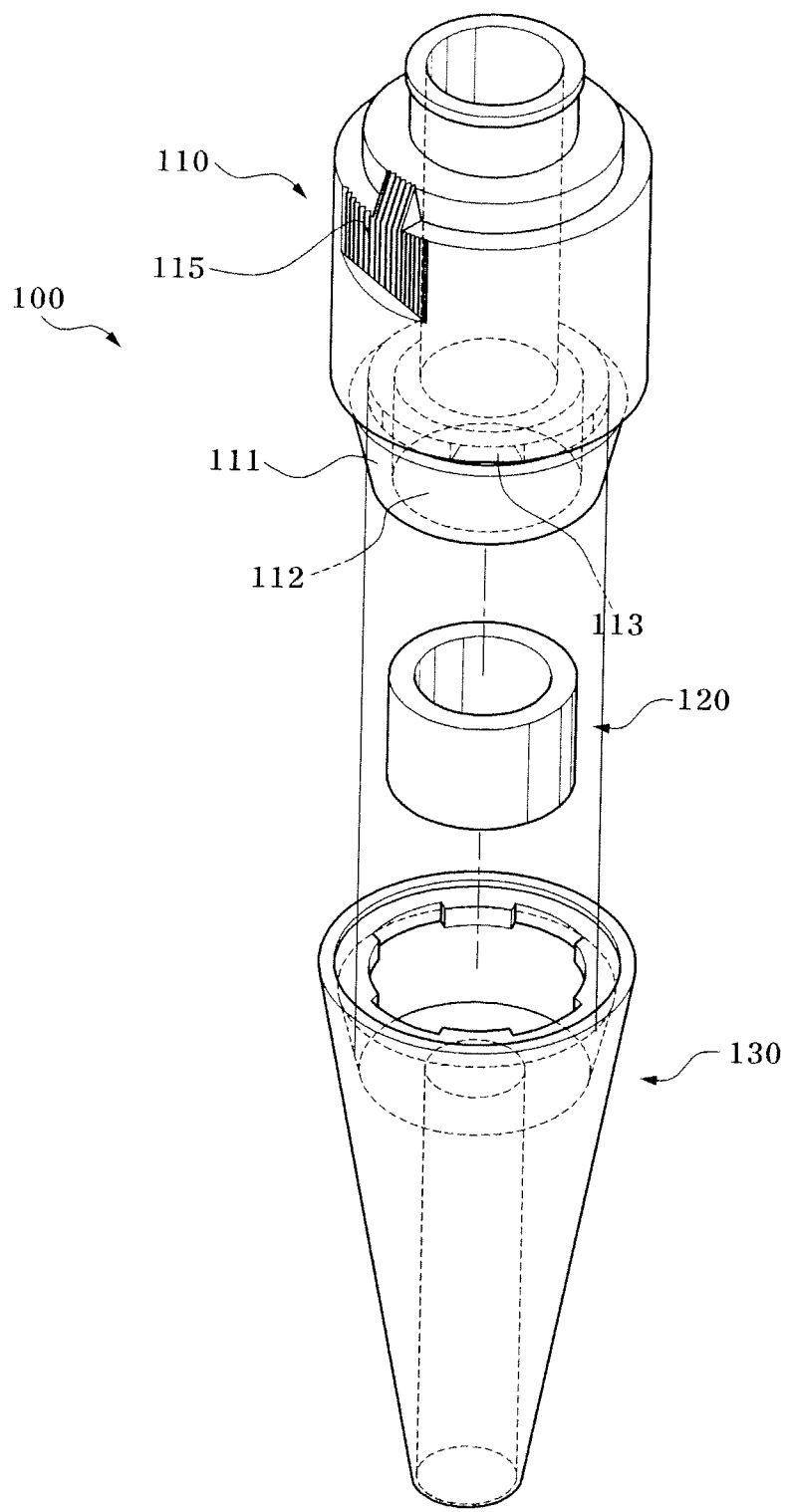
FIG. 1 is an exploded perspective view of a strain relief apparatus of a probe in accordance with one embodiment of the present invention.
Figure 2:
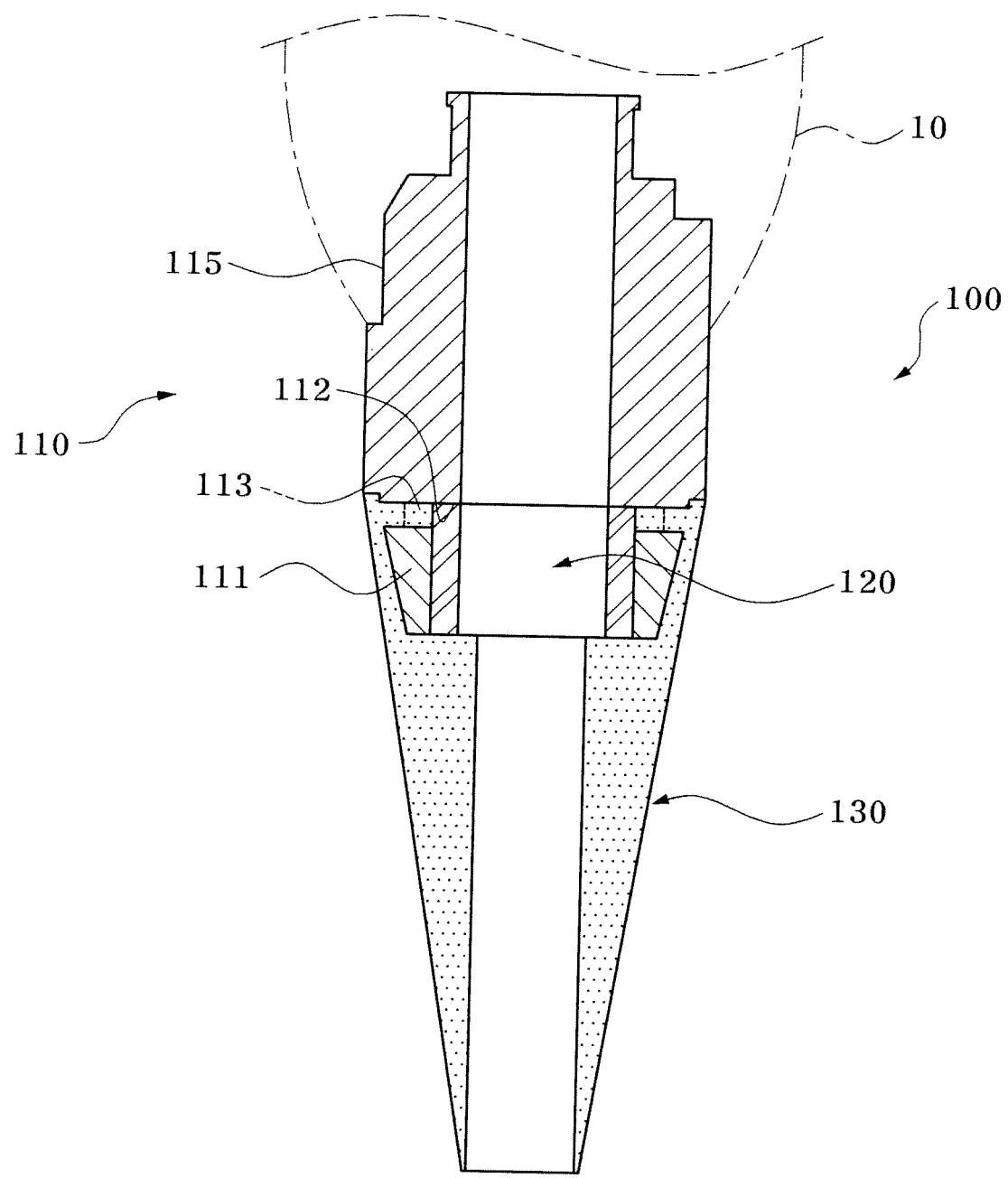
FIG. 2 is a cross-sectional view of the strain relief apparatus in accordance with the embodiment of the present invention.

FIG. 1 is an exploded perspective view of a strain relief apparatus of a probe in accordance with one embodiment of the invention, and FIG. 2 is a cross-sectional view of the strain relief apparatus in accordance with the embodiment of the invention.

Referring to FIGS. 1 and 2, a strain relief apparatus of a probe according to one embodiment includes an insert part 110, a ferrite core 120, and a rubber part 130.

The insert part 110 is mounted on a probe switch box 10. In this embodiment, the insert part 110 has a cylindrical shape with an outer surface bulging outward and is formed therein with a through-hole (reference numeral omitted). The insert part 110 is mounted at one side thereof on the probe switch box 10 and connected at the other side thereof to the rubber part 130.

In this embodiment, the insert part 110 includes an extension portion 111. The extension portion 111 is located at the other side of the insert part 110 and extends towards the rubber part 130. The extension portion 111 has smaller inner and outer diameters than other portions of the insert part 110. As a result, steps are formed at inner and outer borders of the extension portion 111 to the other portions of the insertion part 110.

Moreover, the insert part 110 has an insertion recess 112 at an inner side thereof. The insertion recess 112 is formed inside the insert part 110 having the through-hole to be defined inside the extension portion 111. In this embodiment, the insertion recess 112 is formed by the step, which is formed at the inner border of the extension portion 111, and is open towards the rubber part 130.

A D-cut portion 115 for preventing rotation of the insert part 110 is formed on the insert part 110, that is, on one side of the insert part 110 that will be disposed on the probe switch box 10. In this embodiment, the D-cut portion 115 is depressively formed on an outer circumferential surface of the one side of the insert part 110 and a rear side of the probe switch box 10 coupled to the one side of the insert part 110 has a shape corresponding to that of the outer circumferential surface of the one side of the insert part 110 on which the D-cut portion 115 is formed.

The D-cut portion 115 defines a linear section on the outer circumferential surface of the insert part 110 to prevent the insert part 110 disposed on the probe switch box 10 from rotating on the probe switch box 10.

The ferrite core 120 is mounted on the insertion recess 112. The ferrite core 120 serves to shield electronic-wave noise from escaping a cable (not shown). Since details and operation of the ferrite core 120 are apparent to those skilled in the art, a detailed description thereof will be omitted herein.

According to this embodiment, the ferrite core 120 has a shape corresponding to the shape of the insertion recess 112 and is formed therein with a through-hole (reference numeral omitted), through which the cable can pass. By mounting the ferrite core 120 on the insertion recess 112, the ferrite core 120 is inserted into the insert part 110, and the cable is inserted into the insert part 110 through the through-hole in the ferrite core 120.

The rubber part 130 is provided to the insert part 110 by injection molding. The rubber part 130 is connected to the other side of the insert part 110 by insert-injection molding the rubber part 130 to the extension portion 111. The rubber part 130 is formed by the insert-injection molding to the extension portion 111 by injecting a resin for the rubber part 130 (hereinafter, referred to as the "resin") onto inner and outer sides of the extension portion 111.

Further, the extension portion 111 is formed with an injection groove 113. The injection groove 113 is formed on a lateral side of the extension portion 111 to penetrate the inner and outer sides of the extension portion 111. The rubber part 130 is formed on the extension portion 111 and the injection groove 113 by insert-injection molding.

According to this embodiment, upon injection of the rubber part 130, an outer surface of the extension portion 111 and the injection groove 113 are covered and filled with the resin. The rubber part 130 formed by covering the outer surface of the extension portion 111 and the injection groove 113 with the resin has an increased contact area with the extension portion 111, so that the rubber part 130 is bonded to the insert part 110 with a strong bonding force and is thus prevented from rotating on the insert part 110.

The rubber part 130 is provided to the insert part 110 by insert-injection molding so that a step is not formed on the outer border of the rubber part 130 to the insert part 110. Thus, the insert part 110 and the rubber part 130 are formed such that the outer surfaces thereof provide a single continuous line as seen from a side section view of the strain relief apparatus.

Moreover, the rubber part 130 is formed with a through-hole (reference numeral omitted). A cable connected to a main body of an ultrasonic diagnostic apparatus (not shown) is inserted into the probe switch box 10 through the rubber part 130, ferrite core 120 and insert part 110, all of which have the through-holes therein.

The rubber part 130 may have elasticity to absorb external impact and is made of a flexible material that can be freely bent. The rubber part 130 protects the cable from external impact applied to the cable, and suppresses influence by bending of the cable on a contact point between the probe switch box 10 and the cable.

Figure 3:
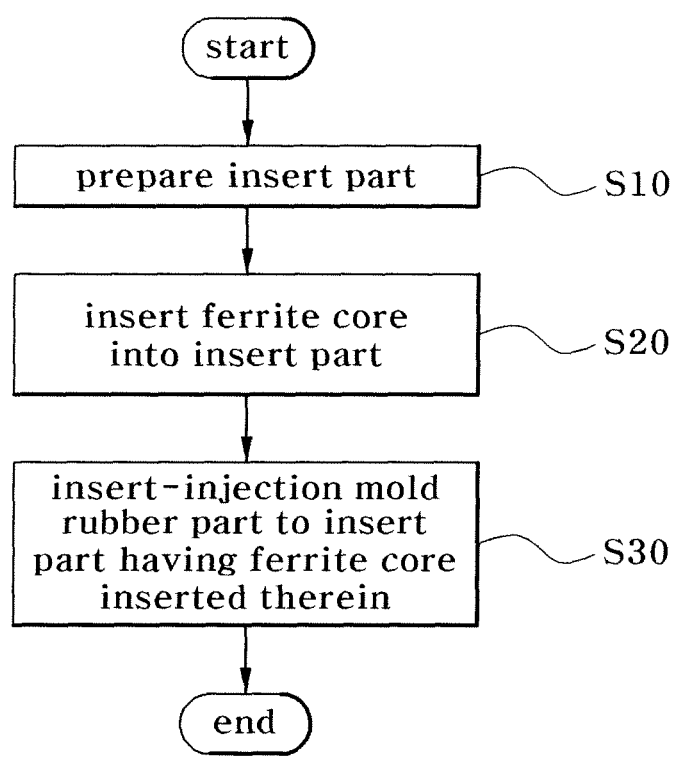
FIG. 3 is a flowchart of a method of manufacturing a strain relief apparatus of a probe in accordance with one embodiment of the present invention.

FIG. 3 is a flowchart of a method of manufacturing a strain relief apparatus of a probe in accordance with one embodiment of the invention.

Next, a method of manufacturing a strain relief apparatus of a probe according to one embodiment will be described with reference to FIGS. 1 to 3.

Referring to FIGS. 1 to 3, to manufacture a strain relief apparatus 100 according to one embodiment, first, an insert part 110 is prepared in S10. The insert part 110 has a hollow cylindrical shape with an outer surface bulging outward and is formed therein with a through-hole.

The insert part 110 has a D-cut portion 115 depressively formed on one side thereof, and an extension portion 111 at the other side thereof. The extension portion 111 is formed at an inner side thereof with an insertion recess 112 into which a ferrite core 120 will be inserted, and is formed at a lateral side thereof with an injection groove 113 through which a rubber part 130 is provided to the insert part 110 by insert-injection molding.

After the insert part 110 is prepared as above, the ferrite core 120 is inserted into the insert part 110. According to this embodiment, the ferrite core 120 is inserted into the insert part 110 by mounting the ferrite core 120 on the insertion recess 112 defined inside the extension portion 111, in S20.

Then, the rubber part 130 is provided to the insert part 110 by insert-injection molding with the ferrite core 120 inserted into the insert part 110, in S30. The rubber part 130 may be provided to the insert part 110 through insert-injection molding by injecting a resin so as to cover the extension portion 111 and fill in the injection groove 113. When provided to the insert part 110 by the insert-injection molding, the rubber part 130 is bonded to the insert part 110 with a strong bonding force and is thus prevented from rotating on the insert part 110.

The strain relief apparatus 100 according to this embodiment manufactured as above protects a cable of an ultrasonic diagnostic apparatus from impact applied to the cable and suppresses influence by bending of the cable on a contact point between a probe switch box and the cable, thereby preventing damage of the cable.

Further, in the strain relief apparatus 100 according to the embodiment, the rubber part 130 is formed to the insert part 110 by insert-injection molding with the ferrite core 120 inserted into the insert part 110, so that the number of components is reduced and separate assembly operation is eliminated, thereby facilitating the fabrication of the apparatus and reducing manufacturing costs.

Further, in the strain relief apparatus 100 according to the embodiment, the insert part 110 is prevented from rotating on the probe switch box 10 and the rubber part 130 is prevented from rotating on the insert part 130, thereby preventing abrasion or damage of the strain relief apparatus 100 caused by rotation and friction between the probe switch box 10, insert part 110 and rubber part 130.

Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. The scope of the invention should be limited only by the accompanying claims.

What is claimed is:

1. A strain relief apparatus of a probe comprising:
    an insert part mounted on a probe switch box and having an insertion recess at an inner side thereof;
    a ferrite core mounted on the insertion recess; and
    a rubber part provided to the insert part by injection molding,
    wherein the insert part comprises an extension portion extending towards the rubber part to define the insertion recess inside the extension portion, and
    the extension portion is formed with an injection groove and the rubber part is formed on the extension portion and the injection groove by insert-injection molding.

2. The strain relief apparatus according to claim 1, wherein the rubber part is provided to the insert part without a step therebetween by the injection molding.

3. The strain relief apparatus according to claim 1, further comprising:
    a D-cut portion formed on one side of the insert part to prevent rotation of the insert part mounted on the probe switch box.

* * * * *